United States Patent [19]
Frazin

[11] Patent Number: 5,836,882
[45] Date of Patent: Nov. 17, 1998

[54] METHOD AND APPARATUS OF LOCALIZING AN INSERTION END OF A PROBE WITHIN A BIOTIC STRUCTURE

[76] Inventor: Leon J. Frazin, 542 Wilgate, Glencoe, Ill. 60022

[21] Appl. No.: 819,602

[22] Filed: Mar. 17, 1997

[51] Int. Cl.⁶ .................................................. A61B 0/00
[52] U.S. Cl. ............................................................ 600/462
[58] Field of Search .................... 128/662.05–662.06, 128/899; 600/462, 471, 441

[56] References Cited

U.S. PATENT DOCUMENTS

| | | | |
|---|---|---|---|
| 3,556,079 | 1/1971 | Omizo | 128/662.05 |
| 4,697,595 | 10/1987 | Breyer et al. . | |
| 4,706,681 | 11/1987 | Breyer et al. . | |
| 4,821,731 | 4/1989 | Martinelli et al. . | |
| 5,095,910 | 3/1992 | Powers | 128/662.05 |
| 5,131,395 | 7/1992 | Gehlbach | 128/662.03 |
| 5,158,088 | 10/1992 | Nelson et al. | 128/662.05 |
| 5,174,295 | 12/1992 | Christian et al. . | |
| 5,203,337 | 4/1993 | Feldman et al. . | |
| 5,329,927 | 7/1994 | Gardineer et al. | 128/662.05 X |
| 5,363,852 | 11/1994 | Sharkawy | 128/662.05 |
| 5,398,691 | 3/1995 | Martin et al. | 128/662.06 |
| 5,546,949 | 8/1996 | Frazin et al. | 128/662.06 |
| 5,549,112 | 8/1996 | Cockburn et al. | 128/662.05 |

*Primary Examiner*—Francis J. Jaworski
*Attorney, Agent, or Firm*—Sonnenschein Nath & Rosenthal

[57] ABSTRACT

A method and apparatus for localizing a tip of a probe inside a biotic structure. The apparatus includes a probe with an ultrasonic transmitter attached proximate a tip of an insertion end of the probe. The apparatus further includes a color Doppler ultrasonic imaging system coupled to a sonifying transducer and a speaker coupled to the ultrasonic imaging system which reproduces sound information indicative of a position of the probe relative to the sonifying transducer.

10 Claims, 1 Drawing Sheet

METHOD AND APPARATUS OF LOCALIZING AN INSERTION END OF A PROBE WITHIN A BIOTIC STRUCTURE

FIELD OF THE INVENTION

The field of the invention relates to probe positioning within organs, cavities or incorporeal conduits (e.g. cardiovascular systems) of living subjects and in particular to the use of acoustic position sensing of probes within the bodies of such subjects.

BACKGROUND

Catheterization of the cardiovascular system may be performed for any of a number of diagnostic and therapeutic reasons. For example, catheterization may be used to implant electrodes of a pacemaker into the heart of a subject needing a pacemaker or for balloon angioplasty where a balloon is inflated in an artery of a subject thereby widening restricted blood vessels. Catheterization is also useful in relation to certain surgical procedures for the repair of damaged blood vessels. Additionally a host of other medical procedures require incorporeal placement of other invasive devices, and precise knowledge of device position within the body.

One difficulty in performing medical procedures involving catheterization lies in guiding the catheter through blood vessels of the cardiovascular system. As the catheter moves through the blood vessel, the catheter is prone to taking "wrong turns" into secondary blood vessels leading away from the target of the intervention.

To solve the problem of locating a probe such as a catheter within a blood vessel, fluoroscopy has been relied upon in conjunction with the use of a contrast medium (e.g., iodine) introduced into the blood of the subject. Fluoroscopy, in fact, has been used since 1950 in retrograde aortic root and left and right ventricle catheterization and angioplasty for accurate catheter guidance.

Other methods of determining a location of a probe inside blood vessels of the cardiovascular system or, alternatively, within the organs of a subject have included ultrasonic imaging techniques. Using ultrasound, sound waves are transmitted from an ultrasonic transducer through the soft tissue of the subject. Upon striking the probe, the sound waves are reflected back to the ultrasonic transducer where the reflected sound waves are detected and an image of the reflecting object is displayed on a monitor.

Two-dimensional ultrasonic images may be displayed on the monitor in a pie-shape format (i.e., in a sector array). Systems used for tissue study typically display an image under a rectangular or square format (i.e., in a linear array) using similar techniques. For the sectored array, the apex of the pie represents the relative position of the ultrasonic transducer and ultrasonically reflecting objects are displayed radially from the apex of the imaging field. Relative positioning of the reflecting object within the display is determined by the length of time required for a reflected sound wave to return to the transducer and from the relative angle of the sound wave with respect to the transducer.

While ultrasonic imaging can provide important information relative to probe position, it is limited in at least two respects. First, ultrasound does not easily pass through bone or lung. More specifically, bone reflects ultrasound sufficiently to mask, and thereby render invisible, important structures lying behind the bone.

Secondly, an ultrasound image (e.g., B-mode) is a two-dimensional display, providing information with respect to a relatively small area of a two-dimensional plane passing through the body. Where a catheter passes orthogonally through the plane, the ultrasonic image may display a small circular shape, representative of the diameter of the probe at some unknown location along its length. By moving the ultrasonic transducer, an operator may be able to obtain more information (i.e., by aligning the plane of the ultrasound image with a longitudinal axis of the probe). However, if the probe and its tube are deflected in more than two dimensions (a highly likely event in most cases) the operator may still not be able to identify an insertion end of the probe. In addition, some cardiac structures, such as valvular apparatus and aortic wall, especially if highly echogenic, can be mistaken as the catheter tip. Because of the importance of catheterizations to heart patients, in general, and tissue study in particular, a need exists for a better method of localizing a probe within a biotic structure.

SUMMARY OF THE INVENTION

Figure 1:
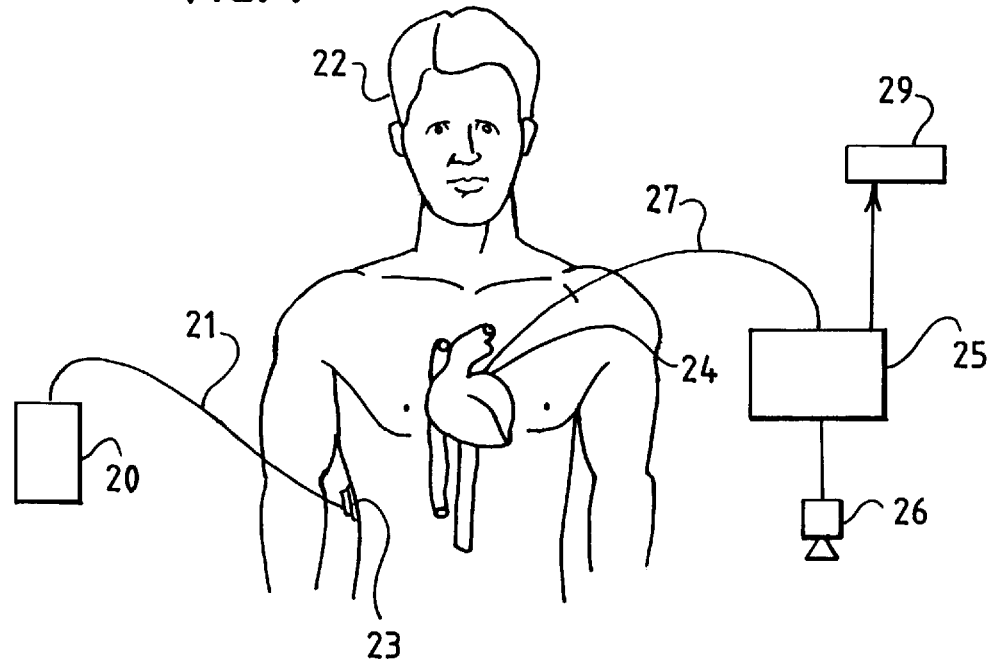
FIG. 1 is a cut-away view of a catheterized subject and catheterization equipment and a velocimetric probe system in accordance with the invention.

A method and apparatus for localizing a tip of a probe inside a biotic structure. The apparatus includes a probe with an ultrasonic transceiver attached proximate a tip of an insertion end of the probe. The apparatus further includes an ultrasonic imaging system coupled to a sonifying transducer and a speaker operatively coupled to the ultrasonic transceiver which reproduces sound information indicative of a position of the probe relative to the sonifying transducer.

BRIEF DESCRIPTION OF THE PREFERRED EMBODIMENT

The solution to the problem of determining a location of an insertion end of a probe within the body of a subject (e.g., within a blood vessel of a heart patient, breast of a breast cancer patient, etc.) lies conceptually in placing a transceiver of a velocimetric detection system at the insertion end of the probe and using an acoustic signal from an ultrasonic transducer of an ultrasonic imaging system (detected by a velocimetric transceiver) as an audio indication of location of the transceiver on the probe with respect to an ultrasonic transducer of the ultrasonic imaging system. An associated speaker of the velocimetric system is used to reproduce a location indicating audio signal from the transceiver on the probe. The probe may be a single device or may be a catheter used to contain and guide other devices. As a further aid in locating the probe, the ultrasonic imaging system may visually display probe location on an ultrasonic monitor based upon reflected acoustic bursts detected by the ultrasonic transducer of the imaging system.

In use, an ultrasonic transducer of the ultrasonic imaging system is located in the same plane as the probe (e.g., on the opposite side of the organ to be catheterized) for transmitting signals to the transceiver. The monitor of the ultrasonic transducer will display structures reflecting sound to the transducer of the imaging system and a speaker located on the velocimeter will provide an audio indication of position of the transceiver relative to the transducer based upon the signal from the transducer of the image system.

It is to be understood that the invention described herein may be applicable to a variety of probes and probing techniques including probes having diagnostic and/or therapeutic utility. Within the cardiovascular system, the invention may be used for guidance of flow velocity probes, pressure measurement probes, myocardial biopsy devices and for electrode probe placement. The invention may also be used for guidance for catheters enabling the delivery of ultrasound contrast material for purposes of determining organ perfusion. It may be used for guidance for intravascular B-mode imaging devices and for balloon dilation devices. Guidance can also be provided for atherectomy, laser, rotablation devices. Tissue aspiration and biopsy needles are further applications. Guidance may be provided for occluder devices such as those used in the treatment of congenital heart disease or acquired intracardiac shunts. Guidance may also be provided for placement of ventricular assist devices.

In the area of OB/GYN, biopsy devices for the breast or chorionic villus may be more accurately located. Aspiration devices for the umbilical cord or amniocentesis are applications.

Gastrointestinal or genitourinary probes for hepatic or kidney or prostate biopsies, prostate radioactive seed implants, respectively, may be more accurately placed under this invention.

Aspiration and biopsy devices for neurosurgical applications are also included.

Under an embodiment of the invention, the transceiver is a piezoelectric element (e.g., a Doppler acoustic transceiver) interconnected with a Doppler standard velocimeter. The velocimeter, in addition to functioning as a power supply in providing an excitation signal to the Doppler transceiver, also beneficially serves to measure and display blood flow on a display 25 during retrograde arterial catheterization. Measurement of blood flow during catheterization ensures the safety of the patient by ensuring that the catheter is advancing in the proper direction. Where the catheter is not advancing in the proper direction (i.e., the catheter has doubled over during insertion) the velocimeter may be used to detect a reversal of blood flow past the Doppler transducer.

The Doppler velocimeter 24, 25, 27 (FIG. 1) may be a Smart Needle manufactured by CardioVascular Dynamics of Irvine, Calif. with a 14 megahertz (MHZ) transceiver excitation frequency. A pulse repetition frequency of 120 kilohertz (Khz) may be used. The Doppler velocimeter may be constructed to successively transmit eight cycle bursts through a transceiver 24 of the probe 27, each followed by a pause, during which the velocimeter listens for echoes and then determines a blood velocity based on those echoes.

Alternatively, the probe 27 may be a three-hole (triple lumen) multipurpose catheter manufactured by USCI/Bard of Billerica, Mass. Two of the lumens (0.61 mm internal diameter) may be used for electrical conductors interconnecting the velocimeter and Doppler transceiver 24 attached to the tip of the catheter 27. The third lumen (1.245 mm internal diameter) may be used for a "J" guide wire and/or for sensing blood pressure. The catheter 27 may also be curved at a 30 degree angle relative to its primary axis at a point 4 cm from its tip.

The ultrasonic transducer and display (ultrasonic imaging system) 20, 21, 23 may be a Model No. 128XP-10 made by Acuson of Mountain View, Calif. A standard Doppler imaging format may be used for color display of anatomical structures causing Doppler frequency shifts.

Turning again to FIG. 1, the catheter tip positioning system is shown in schematic form in conjunction with an outline 22 of a human subject catheterized in accordance with the invention. As shown, a probe 27 having a Doppler transceiver 24 at an insertion end of the probe 27 is inserted into the cardiovascular system of the subject 22 through a sheath inserted into an artery for vascular access. The Doppler transducer 24 on the tip of the probe 27 is interconnected with the velocimeter 25 to monitor blood flow in the catheterized blood vessel during catheterization.

To monitor progress of the tip 24, the ultra-sonic imaging system 20, 21, 23, is used. The sonifying (ultrasound) transducer 23 of the ultrasonic imaging system 20, 21, 23 may be used as a transesophageal, intravascular, transthoracic, transabdominal, transgastric, or transcolonic probe. When the probe is used as a transesophageal probe, the patient is sedated and an ultrasonic transducer 23 is inserted into the throat of the catheterized subject to a position opposite the heart of the patient. The ultrasonic transducer 23 may then be raised, or lowered, or twisted, such that an adequate view of the Doppler transducer 24 is obtained.

In other situations an intravascular probe may be used. An intravascular probe may be used when ultrasonic imaging of the heart is done from the right atrium which may be entered from the superior or inferior vena cava. Intravascular probes may also be placed in the aorta or left ventricle chambers via the brachial or femoral arteries. In either case the intravascular probe (ultrasonic transducer 23) is inserted through the sheath to an appropriate position within the subject.

Where a transthoracic probe is indicated, an ultrasonic transducer 23 is located on an anterior chest wall of the patient and positionally adjusted as appropriate for an adequate view of the Doppler transceiver 24.

Transabdominal, transgastric, or transcolonic probes may be indicated if any of the cardiovascular diagnostic or therapeutic devices are used within abdominal venous or arterial structures.

The ultrasonic imaging system 20, 21, 23 creates an image of the cardiovascular system of the subject 22 by transmitting an ultrasonic pulse from the ultrasonic transducer 23 and then waiting for reflected ultrasonic waves received within a monitored arc (FIG. 2) of a sectored array (or rectangle of a linear array) all within an imaging window of the ultrasonic transducer 23. The imaging window of the ultrasonic transducer 23 may be thought of as a two-dimensional space or plane passing through biotic structure 22 adjacent the ultrasonic transducer 23 and within which ultrasonically reflective objects can be made to appear on a display 20. The ultrasonic imaging system controller 20 determines where to place reflecting objects on a display 20 based upon a receiving angle of a reflected wave and by the elapsed time between transmission of the ultrasonic pulse and receipt of a reflected wave.

Figure 2:
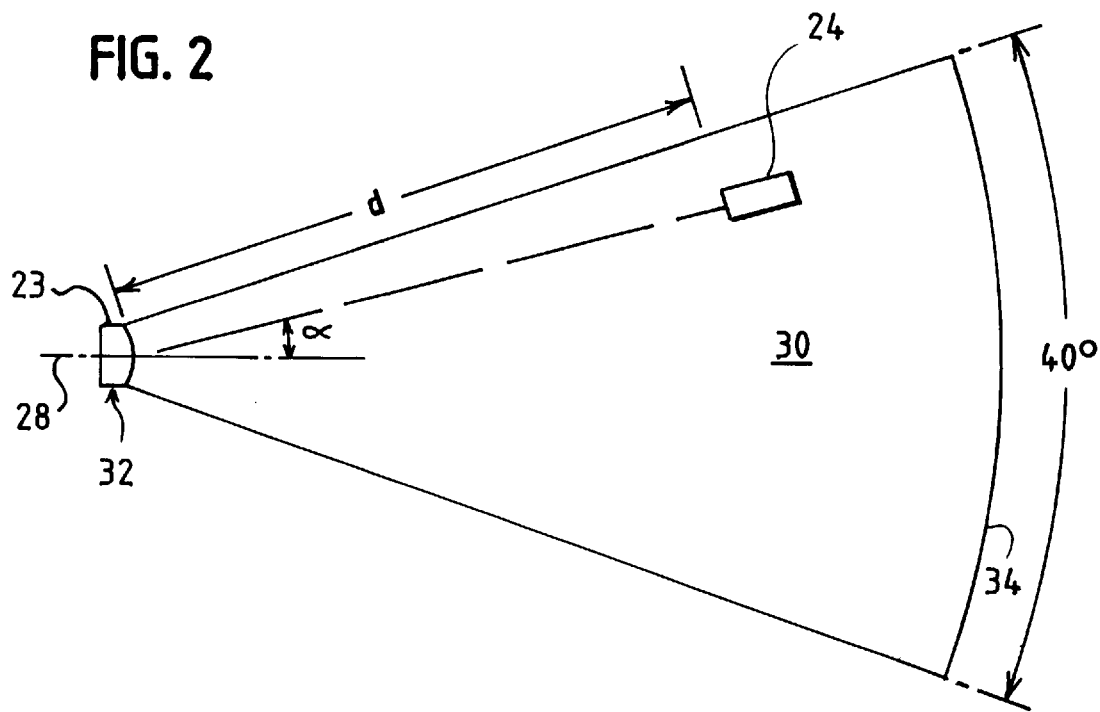
FIG. 2 depicts an imaging window of an ultrasonic imaging system showing the ultrasonic transducer and Doppler transceiver of FIG. 1.

For example, if the ultrasonic transducer 23 were to transmit an ultrasonic pulse and the Doppler transducer 24 (FIG. 2) were at a distance "d" from the ultrasonic transducer, then the transmitted ultrasonic wave would require a time $t_0$ to reach the Doppler transducer 24 and be reflected. An additional time period, $t_0$, would also be required for the reflected wave to return to the ultrasonic transducer 23. If the Doppler transducer were at an angle α from the reference axe's 28 of the ultrasonic transducer 23, the ultrasonic imaging system controller 20 would use the angle of the reflected wave α and time period for receipt of the reflected wave, $2t_0$, to place an image in the proper location (as shown in FIG. 2) of the display 20.

It has been found that when the Doppler transceiver 24 on the tip of the probe 27 is activated, there is an unexpected beneficial interaction between the Doppler transceiver 24 and the ultrasonic imaging system 20, 21, 23. More specifically, it has been found that where the Doppler transceiver 24 is brought near or into the scanning area 30 of the ultrasonic transducer 23 (i.e., within the area of the biotic structure shown on the display 20), an audio speaker 26 begins emitting an audio sound indicator of the distance d of the Doppler transceiver 24 from the ultrasonic transducer 23 (e.g., apex 32 of the scanning area 30). Where the Doppler transceiver 24 is outside of the scanning area 30, there is a lower level of interaction. As the Doppler transceiver 24 is moved towards the ultrasonic transducer 23, the sound emitted by the speaker 26 becomes louder. As the Doppler transceiver 24 is moved away from the ultrasonic transducer 23, the sound becomes fainter, ceasing altogether at some point where the Doppler transceiver 24 has moved past the outside radius 34 of the scanning area 30.

It is believed that the sound emanating from the speaker 26 is caused by an interaction between a sonic pulse from the ultrasonic transducer 23 and the Doppler transceiver 24. While the Doppler transceiver 24 may operate at its own inherent frequency (e.g., 14 MHz) during normal conditions, the impact of an ultrasonic burst from the ultrasonic transducer 23 may cause the Doppler transceiver 24 to momentarily change frequency in sympathetic vibration to the impacting burst from the ultrasonic transducer 23. The result may be a heterodyning of the frequency of the original burst with the natural resonant frequency of the Doppler transducer 24 and in the generation of audible sound through the speaker 26.

To calibrate the sound level emanating from the speaker 26, the ultrasonic transducer 23 and Doppler transceiver 24 may be placed in a tank (not shown) of fluid of a density similar to that of its intended use (e.g., a fluid having a density similar to human tissue). A first sound level may be measured by a sound level meter 29 with the Doppler transceiver 24 placed adjacent the ultrasonic transducer 23 at the apex 32 of the display 30. A second sound level may be measured with the Doppler transducer 24 located at the outer radius 34 of the imaging area 30.

In use, an operator of the ultrasonic imaging system 20, 21, 23 may estimate a location of the Doppler transducer 24 based upon a perceived sound level compared to the first and second sounds detected during calibration. Alternatively, the operator may determine a position quantitatively by reading a current audio level from the meter 29 and comparing the current level with the first and second calibrated levels and extrapolating a position based upon those levels.

The use of the indicating sound from the speaker 26 beneficially allows the tip of the catheter 27 to be located even where a visual image of the Doppler transceiver 24 may not appear in the scanning area 30 due to the presence of an intervening bone structure, or otherwise. The presentation of the sound signal to the speaker 26 for evaluation by the operator allows a relative position of the tip of the catheter 27 to be determined even when a direct visual image would not normally be present, such as when the Doppler transceiver 24 is outside the scanning area 30.

A specific embodiment of novel methods and apparatus for localizing a tip of a catheter according to the present invention have been described for the purpose of illustrating the manner in which the invention is made and used. It should be understood that the implementation of other variations and modifications of the invention and its various aspects will be apparent to one skilled in the art, and that the invention is not limited by the specific embodiments described. Therefore, it is contemplated to cover the present invention and any and all modifications, variations, or equivalents that fall within the true spirit and scope of the basic underlying principles disclosed and claimed herein.

I claim:

1. Apparatus for localizing a tip of a probe relative to a sonifying transducer inside a biotic structure, such apparatus comprising:

a probe with a Doppler transceiver attached proximate a tip of an insertion end of the probe;

a velocimeter power supply coupled to the Doppler transceiver;

an ultrasonic imaging system coupled to a sonifying transducer; and a speaker operatively coupled to the Doppler transceiver which reproduces sound information detected by the Doppler transceiver from an impact on the Doppler transceiver of a sonic wave from the sonifying transducer, which sound is indicative of a position of the probe relative to the sonifying transducer.

2. The apparatus for localizing a tip of a probe inside a biotic structure as in claim 1 wherein the velocimetric power supply further comprises a velocimetric display which displays and instantaneous velocity of fluid surrounding the Doppler transceiver.

3. The apparatus for localizing a tip of a probe inside a biotic structure as in claim 1 further comprising a video display which displays two-dimensional images of sound reflecting structures detected in the imaging window of the sonifying transducer.

4. An apparatus for localizing an insertion end of a probe having therapeutic or diagnostic utility within a biotic structure, such apparatus comprising:

a probe with an ultrasonic transceiver attached proximate a tip of an insertion end of the probe;

a Doppler velocimetric power supply for energizing the ultrasonic transmitter and for providing an instantaneous velocity reading of a fluid surrounding the probe;

a sonifying transducer;

an ultrasonic imaging system coupled to the sonifying transducer; and a speaker coupled to the Doppler transceiver system which reproduces sound information indicative of a position of the probe relative to the sonifying transducer.

5. The apparatus for localizing an insertion end of a probe as in claim 4 further comprising a video display which displays two-dimensional images of sound reflecting structures adjacent the sonifying transducer.

6. The apparatus for localizing an insertion end of a probe as in claim 4 wherein the Doppler velocimetric power supply further comprises a power supply operating at 14 MHZ.

7. The apparatus for localizing an insertion end of a probe as in claim 4 wherein the ultrasonic transceiver further comprises a piezoelectric element.

8. An apparatus for localizing an insertion end of a probe having therapeutic or diagnostic utility within a biotic structure, such apparatus comprising:

a probe with an ultrasonic transceiver attached proximate a tip of an insertion end of the probe;

a Doppler velocimetric power supply for energizing the ultrasonic transceiver;

a sonifying transducer;

a color Doppler ultrasonic imaging system coupled to the sonifying transducer, which displays two-dimensional images of acoustic reflecting structures adjacent the sonifying transducer; and a sound transducer coupled to the ultrasonic transceiver which reproduces audio sound information indicative of a position of the probe relative to the sonifying transducer.

9. The apparatus for localizing an insertion end of a probe as in claim 8 wherein the Doppler velocimetric power supply further comprises a power supply operating at 14 MHZ.

10. The apparatus for localizing an insertion end of a probe as in claim 8 wherein the ultrasonic transmitter further comprises a piezoelectric element.

* * * * *